US011608507B2

(12) United States Patent
Durham et al.

(10) Patent No.: US 11,608,507 B2
(45) Date of Patent: Mar. 21, 2023

(54) TOMATO PLANTS WITH RESISTANCE TO MI-1 RESISTANCE-BREAKING ROOT-KNOT NEMATODES

(71) Applicant: SEMINIS VEGETABLE SEEDS, INC., St. Louis, MO (US)

(72) Inventors: Kelli M. Durham, Sacramento, CA (US); Susana García Andrés, Almeria (ES); Maria Dolores Hernandez, Roldán (ES); Scott J. Huesgen, St. Louis, MO (US); Andrea K. Knox, Sacramento, CA (US); Bram Rozier, Dordrecht (NL); Menno Ter Maat, Bergschenhoek (NL); Sjoerd van der Ent, Capelle aan den IJssel (NL); Ruth A. Wagner, Chesterfield, MO (US)

(73) Assignee: Seminis Vegetable Seeds, Inc., St. Louis, MO (US)

( * ) Notice: Subject to any disclaimer, the term of this patent is extended or adjusted under 35 U.S.C. 154(b) by 0 days.

(21) Appl. No.: 17/095,382

(22) Filed: Nov. 11, 2020

(65) Prior Publication Data
US 2021/0207164 A1     Jul. 8, 2021

Related U.S. Application Data

(60) Provisional application No. 62/957,729, filed on Jan. 6, 2020.

(51) Int. Cl.
*C12N 15/82* (2006.01)
*A01H 6/82* (2018.01)

(52) U.S. Cl.
CPC ......... *C12N 15/8285* (2013.01); *A01H 6/825* (2018.05)

(58) Field of Classification Search
CPC ................................. C12N 15/8285
See application file for complete search history.

(56) References Cited

U.S. PATENT DOCUMENTS

| 2010/0212048 A1* | 8/2010 | Hoogstraten | A01H 5/08 800/301 |
| 2016/0165824 A1* | 6/2016 | Fukunaga | A01H 5/08 800/265 |

FOREIGN PATENT DOCUMENTS

| WO | 2013/095125 | 6/2013 |

OTHER PUBLICATIONS

Takei et al. (De novo genome assembly of two tomato ancestors, Solanum pimpinellifolium and Solanum lycopersicum var. cerasiforme, by long-read sequencing. DNA Research, p. 1-9, 2021) (Year: 2021).*

El-Sappah et al (Tomato Natural Resistance Genes in Controlling the Root-Knot Nematode. Genes. 10, 925, 1-19, 2019) (Year: 2019).*
Tomato Genome Sequencing Consortium_2014 (Year: 2014).*
Tomato Genome Consortium (The tomato genome sequence provides insights into fleshy fruit evolution. Nature 485: 635-641, 2012) (Year: 2012).*
Aoki (Large-scale analysis of full-length cDNAs from the tomato (*Solanum lycopersicum*) cultivar Micro-Tom, a reference system for the Solanaceae genomics. I. BMC Genomics 11:210, p. 1-16, 2010) (Year: 2010).*
Kevei et al. (Resequencing at 140-Fold Depth of the Parental Genomes of a Solanum lycopersicum x S. pimpinellifolium Recombinant Inbred Line Population and Characterization of Frame-Shift InDels That Are Highly Likely to Perturb Protein Function. G3 Genes Genomes Genetics. 5, 971-981, 2015) (Year: 2015).*
Wang et al (Genome of Solanum pimpinellifolium provides insights into structural variants during tomato breeding. Nature Communication. 1-11, 2020) (Year: 2020).*
International Search Report and Written Opinion for International Application No. PCT/US2020/065525, dated May 28, 2021.
Ilarduya et al., The tomato Rme1 locus is required for Mi-1-mediated resistance to root-knot nematodes and the potato aphid, The Plant Journal 27(5):417-425, 2001.
Wang et al., Mapping of a heat-stable gene for resistance to southern root-knot nematode in Solanum lycopersicum, Plant Molecular Biology Reporter 31 (2): 352-362, 2013.
Ammiraja et al., "The heat-stable root-knot nematode resistance gene Mi-9 from Lycopersicon peruvianum is localized on the short arm of chromosome 6," Theor Appl Genet (2003) 106: 478-484.
Jablonska et al., "The Mi-9 Gene from Solanum arcanum Conferring Heat-Stable Resistance to Root-Knot Nematodes Is a Homolog of Mi-1," Plant Physiology (2007) 143: 1044-1054.
Cortada et al., "The Resistance Response of Solanum Huaylasense Accession LA1358 to Meloidogyne SPP.," Nematropica (2010) 40: 31-40.
Davies et al., "Resistance genes against plant-parasitic nematodes: a durable control strategy?" Nematology (2015) 17: 249-263.
Iberkleid et al., "Responses of Tomato Genotypes to Avirulent and Mi-Virulent Meloidogyne javanica Isolates Occurring in Israel," Phytopathology (2014) 104(5):484-96.
Seah et al., "Introgressed and endogenous Mi-1 gene clusters in tomato differ by complex rearrangements in flanking sequences and show sequence exchange and diversifying selection among homologues," Theor Appl Genet (2007) 114:1289-1302.

(Continued)

*Primary Examiner* — Charles Logsdon
*Assistant Examiner* — Wayne Zhong
(74) *Attorney, Agent, or Firm* — Dentons US LLP; Matthew Madsen

(57) ABSTRACT

The present disclosure provides cultivated tomato plants exhibiting increased resistance to Mi-1 resistance-breaking root-knot nematodes. Such plants comprise novel recombinant chromosomal segments comprising alleles associated with disease resistance from *Solanum pimpinellifolium* on chromosome 1 and/or chromosome 6. In certain aspects, compositions and methods for producing, breeding, detecting, and selecting plants or germplasm with an increased disease resistance phenotype are provided.

20 Claims, 2 Drawing Sheets
Specification includes a Sequence Listing.

(56) References Cited

OTHER PUBLICATIONS

Seifi et al., "Linked, if Not the Same, Mi-1 Homologues Confer Resistance to Tomato Powdery Mildew and Root-Knot Nematodes," MPMI vol. 24, No. 4, 2011, pp. 441-450.

Yaghoobi et al., "Fine mapping of the nematode resistance gene Mi-3 in Solanum peruvianum and construction of a S. lycopersicum DNA contig spanning the locus," Mol Gen Genomics (2005) 274: 60-69.

Tzortzakakis, et al., "Occurrence of a new resistant breaking pathotype of Meloidogyne incognita on tomato in Greece," Journal of Plant Diseases and Protection (2014) 121: 184-186.

Tzortzakakis, et al., "Occurrence of a resistant breaking pathotype of Meloidogyne javanica on tomato in Crete, Greece," Fundam. appl. Nematol. (1996) 19(3): 283-288.

Tzortzakakis, et al., "An update on the occurrence of resistance-breaking populations of root-knot nematodes (*Meloidogyne* spp.) on resistant tomato in Greece with six new records from Crete," Hellenic Plant Protection Journal (2016) 9: 60-65.

\* cited by examiner

A: Root development scale

B: Nematode infection visual scale

TOMATO PLANTS WITH RESISTANCE TO MI-1 RESISTANCE-BREAKING ROOT-KNOT NEMATODES

CROSS-REFERENCE TO RELATED APPLICATIONS

This application claims the benefit of priority of U.S. Provisional Application No. 62/957,729, filed Jan. 6, 2020, the disclosure of which is hereby incorporated by reference in its entirety.

FIELD OF THE INVENTION

The present invention relates to the field of agriculture and more specifically to methods and compositions for producing tomato plants exhibiting improved resistance to Mi-1 resistance-breaking root-knot nematodes, and also exhibiting increased root vigor.

INCORPORATION OF SEQUENCE LISTING

The sequence listing that is contained in the file named "SEMB029US_ST25.txt", which is 16.0 kilobytes as measured in Microsoft Windows operating system and was created on Nov. 10, 2020, is filed electronically herewith and incorporated herein by reference.

BACKGROUND OF THE INVENTION

Root-knot nematodes (RKN) are a cause of significant yield loss and plant death in commercial tomato crops. RKN resistance is therefore an important trait in tomato production. Although RKN resistance alleles have been identified in non-cultivated tomato species, efforts to introduce these alleles into cultivated lines are hindered by a lack of specific markers linked to the alleles, linkage drag that leads to unacceptable plant quality, and a lack of broad spectrum resistance. The use of marker-assisted selection (MAS) in plant breeding methods has made it possible to select plants based on genetic markers linked to traits of interest. However, accurate markers for identifying or tracking desirable traits in plants are frequently unavailable even if a gene associated with the trait has been characterized. These difficulties are further complicated by factors such as polygenic or quantitative inheritance, epistasis and an often incomplete understanding of the genetic background underlying expression of a desired phenotype.

SUMMARY OF THE INVENTION

The present invention provides a cultivated tomato plant comprising a first recombinant chromosomal segment from *Solanum pimpinellifolium* on chromosome 1 or chromosome 6, wherein said recombinant chromosomal segment comprises an allele that confers increased resistance to Mi-1 resistance-breaking root-knot nematode species relative to a plant lacking said recombinant chromosomal segment. In some embodiments, the plant further comprises a second recombinant chromosomal segment from *Solanum pimpinellifolium* on chromosome 1 or chromosome 6, wherein said second recombinant chromosomal segment comprises an allele that confers increased resistance to Mi-1 resistance-breaking root-knot nematode species relative to a plant lacking said second recombinant chromosomal segment. In other embodiments, said first recombinant chromosomal segment comprises a marker locus selected from the group consisting of marker locus M2 (SEQ ID NO:1), marker locus M11 (SEQ ID NO:6), marker locus M12 (SEQ ID NO:7), marker locus M13 (SEQ ID NO:8), and marker locus M3 (SEQ ID NO:9) on chromosome 1. In certain embodiments, said Mi-1 resistance-breaking root-knot nematode species resistance allele is located between 82,703,136 bp and 83,446,695 bp on chromosome 1 of the public tomato genome sequence SL3.0. In some embodiments, said first recombinant chromosomal segment comprises a marker locus selected from the group consisting of marker locus M6 (SEQ ID NO:10), marker locus M7 (SEQ ID NO:11), marker locus M8 (SEQ ID NO:16), marker locus M9 (SEQ ID NO:21), and marker locus M10 (SEQ ID NO:26) on chromosome 6. In other embodiments, said Mi-1 resistance-breaking root-knot nematode species resistance allele on chromosome 6 is located between 2,076,193 bp and 2,842,551 bp of the public tomato genome sequence SL3.0. In further embodiments, the plant is homozygous for said recombinant chromosomal segment. In some embodiments, said resistance comprises resistance to nematode species *Meloidogyne javanica*, *Meloidogyne incognita*, or *Meloidogyne enterolobii*. In further embodiments, said resistance comprises resistance to nematode species *Meloidogyne javanica*. In additional embodiments, a sample of seed comprising said Mi-1 resistance-breaking root-knot nematode species resistance allele was deposited under ATCC Accession Number PTA-126291.

The present invention additionally provides a seed that produces a cultivated tomato plant comprising a first recombinant chromosomal segment from *Solanum pimpinellifolium* on chromosome 1 or chromosome 6, wherein said recombinant chromosomal segment comprises an allele that confers increased resistance to Mi-1 resistance-breaking root-knot nematode species relative to a plant lacking said recombinant chromosomal segment.

The present invention provides a plant part of a cultivated tomato plant comprising a first recombinant chromosomal segment from *Solanum pimpinellifolium* on chromosome 1 or chromosome 6, wherein said recombinant chromosomal segment comprises an allele that confers increased resistance to Mi-1 resistance-breaking root-knot nematode species relative to a plant lacking said recombinant chromosomal segment. In certain embodiments, the plant part is a cell, a seed, a root, a stem, a leaf, a fruit, a flower, or pollen.

The present invention provides a cultivated tomato plant comprising a first recombinant chromosomal segment from *Solanum pimpinellifolium* on chromosome 1 and a second recombinant chromosomal segment from *Solanum pimpinellifolium* on chromosome 6, wherein said first and second recombinant chromosomal segments comprise an allele that confers further increased resistance to Mi-1 resistance-breaking root-knot nematode species relative to a plant lacking said first or second recombinant chromosomal segment, and wherein said first and second recombinant chromosomal segments confer increased root vigor relative to a plant lacking said first and second recombinant chromosomal segments. In some embodiments, the plant is homozygous for said first or second recombinant chromosomal segment.

The present invention also provides a method for producing a cultivated tomato plant with improved resistance to Mi-1 resistance-breaking root-knot nematode species, comprising introgressing into said plant a Mi-1 resistance-breaking root-knot nematode species resistance allele from *Solanum pimpinellifolium* within a recombinant chromosomal segment flanked in the genome of said plant by marker locus M2 (SEQ ID NO:1) and marker locus M3

(SEQ ID NO:9) on chromosome 1 or by marker locus M6 (SEQ ID NO:10) and marker locus M10 (SEQ ID NO:26) on chromosome 6, wherein said introgressed Mi-1 resistance-breaking root-knot nematode species resistance allele confers to said plant resistance to Mi-1 resistance-breaking root-knot nematode species relative to a plant lacking said allele. In some embodiments, said plant further comprises a second introgressed Mi-1 resistance-breaking root-knot nematode species resistance allele from *Solanum pimpinellifolium* within a recombinant chromosomal segment flanked in the genome of said plant by marker locus M2 (SEQ ID NO:1) and marker locus M3 (SEQ ID NO:9) on chromosome 1 or by marker locus M6 (SEQ ID NO:10) and marker locus M10 (SEQ ID NO:26) on chromosome 6. In certain embodiments, said introgressing comprises: a) crossing a plant comprising said recombinant chromosomal segment with itself or with a second cultivated tomato plant of a different genotype to produce one or more progeny plants; and b) selecting a progeny plant comprising said recombinant chromosomal segment. In other embodiments, said introgressing comprises backcrossing, marker-assisted selection, or assaying for said resistance to Mi-1 resistance-breaking root-knot nematode species. In further embodiments, selecting a progeny plant comprises detecting nucleic acids comprising: a) marker locus M2 (SEQ ID NO:1), marker locus M11 (SEQ ID NO:6), marker locus M12 (SEQ ID NO:7), marker locus M13 (SEQ ID NO:8), and marker locus M3 (SEQ ID NO:9) on chromosome 1; or b) marker locus M6 (SEQ ID NO:10), marker locus M7 (SEQ ID NO:11), marker locus M8 (SEQ ID NO:16), marker locus M9 (SEQ ID NO:21), and marker locus M10 (SEQ ID NO:26) on chromosome 6. In yet further embodiments, said backcrossing comprises from 2-7 generations of backcrosses. In additional embodiments, said resistance comprises resistance to nematode species *Meloidogyne javanica*, *Meloidogyne incognita*, or *Meloidogyne enterolobii*. In further embodiments, said resistance comprises resistance to nematode species *Meloidogyne javanica*. In additional embodiments, the progeny plant is an $F_2$-$F_6$ progeny plant. The present invention further provides cultivated tomato plants obtainable by the methods provided herein.

The present invention also provides a method of selecting a cultivated tomato plant exhibiting resistance to Mi-1 resistance-breaking root-knot nematode species, comprising: a) crossing a cultivated tomato plant comprising a first recombinant chromosomal segment from *Solanum pimpinellifolium* on chromosome 1 or chromosome 6, wherein said recombinant chromosomal segment comprises an allele that confers increased resistance to Mi-1 resistance-breaking root-knot nematode species relative to a plant lacking said recombinant chromosomal segment with itself or with a second cultivated tomato plant of a different genotype to produce one or more progeny plants or crossing a cultivated tomato plant comprising a first recombinant chromosomal segment from *Solanum pimpinellifolium* on chromosome 1 and a second recombinant chromosomal segment from *Solanum pimpinellifolium* on chromosome 6, wherein said first and second recombinant chromosomal segments comprise an allele that confers further increased resistance to Mi-1 resistance-breaking root-knot nematode species relative to a plant lacking said first or second recombinant chromosomal segment, and wherein said first and second recombinant chromosomal segments confer increased root vigor relative to a plant lacking said first and second recombinant chromosomal segments with itself or with a second cultivated tomato plant of a different genotype to produce one or more progeny plants; and b) selecting a progeny plant comprising said Mi-1 resistance-breaking root-knot nematode species resistance allele. In some embodiments, selecting said progeny plant comprises detecting a marker locus genetically linked to said Mi-1 resistance-breaking root-knot nematode species resistance allele. In other embodiments, selecting said progeny plant comprises detecting a marker locus within or genetically linked to a chromosomal segment flanked in the genome of said plant by marker locus M2 (SEQ ID NO:1) and marker locus M3 (SEQ ID NO:9) on chromosome 1 or by marker locus M6 (SEQ ID NO:10) and marker locus M10 (SEQ ID NO:26) on chromosome 6. In additional embodiments, selecting said progeny plant comprises detecting nucleic acids comprising: a) marker locus M2 (SEQ ID NO:1), marker locus M11 (SEQ ID NO:6), marker locus M12 (SEQ ID NO:7), marker locus M13 (SEQ ID NO:8), and marker locus M3 (SEQ ID NO:9) on chromosome 1; or b) marker locus M6 (SEQ ID NO:10), marker locus M7 (SEQ ID NO:11), marker locus M8 (SEQ ID NO:16), marker locus M9 (SEQ ID NO:21), and marker locus M10 (SEQ ID NO:26) on chromosome 6. In some embodiments, the progeny plant is an $F_2$-$F_6$ progeny plant. In other embodiments, producing said progeny plant comprises backcrossing.

BRIEF DESCRIPTION OF THE DRAWINGS

FIG. 1A. Shows the scale for visually scoring root development, where 1 refers to a highly developed root system and 9 refers to the least developed root system. FIG. 1B. Shows the scale for visual determination of nematode infection, where 1 refers to no infection and 9 refers to heavily infected roots with many galls.

DETAILED DESCRIPTION

Figure 1:
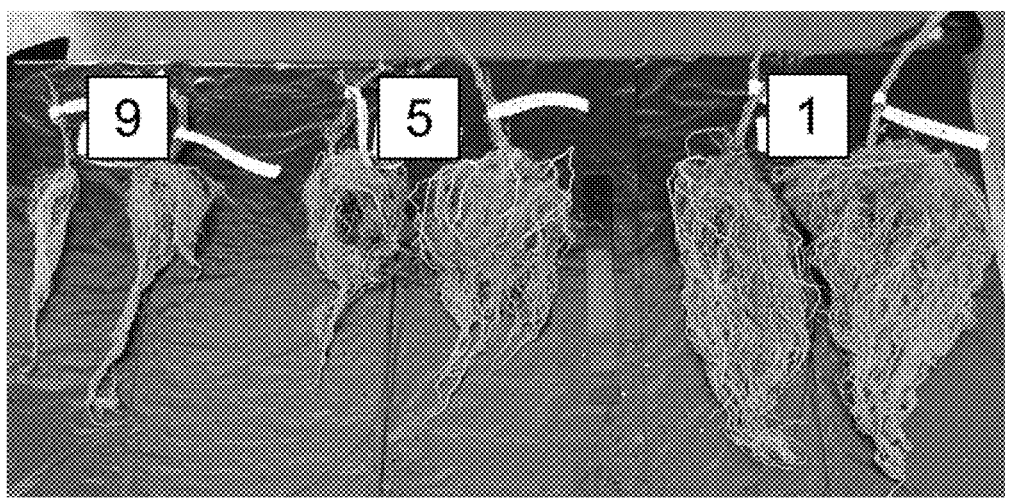
FIG. 1: Shows scales for scoring visual root traits.
Figure 1:
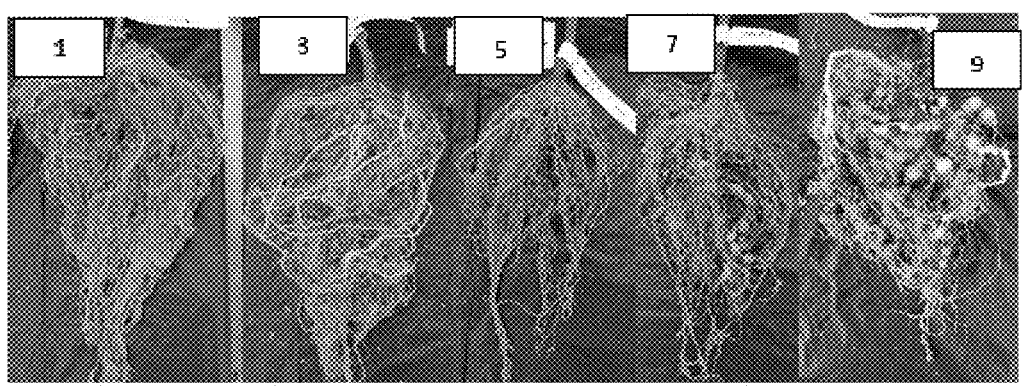

Tomato (*Solanum lycopersicum*) is an important commercial crop across the world. There are many pests and diseases that damage both quality and quantity of tomato production. Among these pests are root-knot nematodes (RKN). These nematodes of the genus *Meloidogyne* can damage the root system of tomato plants severely, resulting in reduced plant vigor leading to significantly reduced tomato production or even total loss of the crop. In the *Meloidogyne* genus four species (*Meloidogyne incognita*, *Meloidogyne javanica*, *Meloidogyne arenaria*, and *Meloidogyne hapla*) are considered the major causes of crop damage, while two species (*Meloidogyne enterolobii* and *Meloidogyne chitwoodi*) are considered emerging pests.

Some loci have been identified that provide resistance to RKN. So far, only the Mi-1 gene, which is located on chromosome 6, has been successfully used in commercial tomatoes and is often used as the benchmark for resistance. Several other RKN resistance genes have been mapped to the same location. One of these is Mi-9, a heat-stable gene that provides resistance to the same set of RKN isolates, but has yet to be made available for breeding into elite germplasm. As Mi-1 has been adopted for commercial use, RKN isolates have emerged that overcome the resistance provided by the Mi-1 gene. From the known resistance loci, Mi-3, which is located on chromosome 12, provides resistance against isolates that break Mi-1 resistance. However, the source for Mi-3 is *Solanum peruvianum* and has yet to be successfully bred into *Solanum lycopersicum* germplasm. Mi-1 resistance-breaking RKN resistance conferred by a single locus on chromosome 4 has also been described, but the original source of this locus is unclear.

The present invention represents a significant advance in that it provides a *Solanum pimpinellifolium* source (LA1257) that contains loci conferring resistance against RKN that break the Mi-1 resistance. These are the first RKN resistance loci that have been identified in *Solanum pimpinellifolium*. Interestingly, these loci not only confer resistance against Mi-1 resistance-breaking nematode isolates, they also increase the vigor with which the root system grows. This is an important trait for tomato breeders, and especially tomato rootstock breeders, as a larger root system allows for a longer productive life of the tomato plant.

I. GENOMIC REGIONS, ALLELES, AND POLYMORPHISMS ASSOCIATED WITH INCREASED RESISTANCE TO MI-1-BREAKING RKN

The inventors identified two novel QTLs (one on chromosome 1 and one on chromosome 6) from *Solanum pimpinellifolium* that provide resistance to Mi-1-breaking RKN isolates. These isolates are generally *Meloidogyne javanica* isolates, but resistance is also observed against *Meloidogyne incognita* isolates and some unidentified isolates. The novel resistance is currently most effective against isolates collected in countries of the Mediterranean region. At the same time, the QTLs increase the root vigor of tomato plants.

The newly identified QTL on chromosome 6 covers a region of 0.3 cM and maps to the same region as the Mi-1 locus. However, data provided herein show that the newly identified QTL confers resistance to Mi-1 resistance-breaking isolates from the root knot nematode species *Meloidogyne javanica* and *Meloidogyne incognita*. The newly identified QTL on chromosome 6 is flanked by M6, a SNP change [C/G] at 2,076,193 bp on the publicly available tomato genome SL3.0, which can be found at solgenomics-.net, and M10, a SNP change [A/G] at 2,842,551 bp. Interstitial markers, such as M7, a SNP change [A/G] at 2,519,127 bp, M8, a SNP change [C/A] at 2,633,793 bp, and M9, a SNP change [A/G] at 2,381634 bp, can be used in addition to the flanking markers to select for the resistance QTL on chromosome 6. Thus, the present disclosure provides an elite or cultivated tomato plant comprising a recombinant chromosomal segment from *Solanum pimpinellifolium* flanked by markers M6 and M10 on chromosome 6 that comprises an allele that confers increased resistance to resistance-breaking RKN. In certain embodiments, one or both of the flanking markers are interstitial markers between M6 and M10, such as markers M7, M8, and M9.

The QTL on chromosome 1 covers a region of 2.0 cM which is situated between M2, a SNP change [A/C] at 82,703,136 bp, and M3, a SNP change [G/T] at 83,446,695 bp. Interstitial markers, such as M11, a SNP change [C/G] at 82,711,231 bp, M12, a SNP change [TIC] at 82,992,118 bp, or M13, a SNP change [C/T] at 83,278,437 bp, can be used in addition to the flanking markers to select for the resistance QTL on chromosome 1. Thus, the present disclosure provides an elite or cultivated tomato plant comprising a recombinant chromosomal segment from *Solanum pimp-inellifolium* flanked by markers M2 and M3 on chromosome 1 that comprises an allele that confers increased resistance to resistance-breaking RKN. In certain embodiments, one or both of the flanking markers are interstitial markers between M2 and M3, such as markers M11, M12, and M13.

II. INTROGRESSION OF GENOMIC REGIONS ASSOCIATED WITH DISEASE RESISTANCE

Marker-assisted introgression involves the transfer of a chromosomal region defined by one or more markers from a first genetic background to a second. Offspring of a cross that contain the introgressed genomic region can be identified by the combination of markers characteristic of the desired introgressed genomic region from a first genetic background and both linked and unlinked markers characteristic of the second genetic background.

The present invention provides novel markers for identifying and tracking introgressions of one or more of the genomic regions from a resistance source, which could be any tomato plant, such as any *Solanum pimpinellifolium* plant, into cultivated *Solanum lycopersicum* lines. *Solanum pimpinellifolium* LA1257 is available from the Tomato Genetic Resource Center in Davis, USA, and from the ATCC under Accession No. PTA-126291. The invention further provides markers for identifying and tracking the novel introgressions disclosed herein during plant breeding.

The present invention provides newly identified QTLs that provide resistance to a Mi-1-breaking RKN isolate. As used herein, the term "Mi-1-breaking RKN isolate" refers to an RKN isolate capable of causing a disease in a tomato plant that has a Mi-1 gene, e.g., Nemato.

Markers within or linked to any of the genomic intervals of the present invention can be used in a variety of breeding efforts that include introgression of genomic regions associated with disease resistance into a desired genetic background. For example, a marker within 30 cM, 25 cM, 20 cM, 16 cM, 15 cM, 10 cM, 5 cM, 2 cM, or 1 cM of a marker associated with disease resistance described herein can be used for marker-assisted introgression of genomic regions associated with a disease resistant phenotype.

*Solanum lycopersicum* plants comprising one or more recombinant chromosomal segments associated with a desired phenotype wherein at least 10%, 25%, 50%, 75%, 90%, or 99% of the remaining genomic sequences carry markers characteristic of the germplasm are also provided. *Solanum lycopersicum* plants comprising a recombinant chromosomal segment comprising regions closely linked to or adjacent to the genomic regions and markers provided herein and associated with an Mi-1-breaking RKN resistance phenotype and/or an increased root vigor phenotype are also provided.

III. DEVELOPMENT OF DISEASE RESISTANT SOLANUM LYCOPERSICUM VARIETIES

For most breeding objectives, commercial breeders work within germplasm that is "cultivated type" or "elite." This germplasm is easier to breed because it generally performs well when evaluated for horticultural performance. For example, *Solanum lycopersicum* is an agronomically elite, cultivated tomato species adapted to commercial use. However, the performance advantage a cultivated germplasm provides can be offset by a lack of allelic diversity. Breeders generally accept this tradeoff because progress is faster when working with cultivated material than when breeding with genetically diverse sources.

In contrast, when cultivated germplasm is crossed with non-cultivated germplasm, a breeder can gain access to novel alleles from the non-cultivated type. However, this approach presents significant difficulties due to fertility problems associated with crosses between diverse lines, and negative linkage drag from the non-cultivated parent. In tomato plants, non-cultivated types such as *Solanum peruvianum* and *Solanum pimpinellifolium*, can provide alleles associated with disease resistance. However, these non-cultivated species may have poor horticultural qualities such as vulnerability to necrosis or low fruit production.

The process of introgressing desirable resistance genes from non-cultivated lines into elite cultivated lines while avoiding problems with linkage drag or low heritability is a long and often arduous process. Success in deploying alleles derived from wild relatives therefore strongly depends on minimal or truncated introgressions that lack detrimental effects and reliable marker assays that replace phenotypic screens. Success is further defined by simplifying genetics for key attributes to allow focus on genetic gain for quantitative traits such as disease resistance. Moreover, the process of introgressing genomic regions from non-cultivated lines can be greatly facilitated by the availability of informative markers.

One of skill in the art would therefore understand that the alleles, polymorphisms, and markers provided by the invention allow the tracking and introduction of any of the genomic regions identified herein into any genetic background. In addition, the genomic regions associated with disease resistance disclosed herein can be introgressed from one genotype to another and tracked phenotypically or genetically. Thus, Applicants' discovery of accurate markers associated with disease resistance will facilitate the development of tomato plants having beneficial phenotypes. For example, plants and seeds can be genotyped using the markers of the present invention in order to develop varieties comprising desired disease resistance. Moreover, marker-assisted selection (MAS) allows identification of plants which are homozygous or heterozygous the desired introgression.

Meiotic recombination is essential for plant breeding because it enables the transfer of favorable alleles across genetic backgrounds, the removal of deleterious genomic fragments, and pyramiding traits that are genetically tightly linked. In the absence of accurate markers, limited recombination forces breeders to enlarge segregating populations for progeny screens. Moreover, phenotypic evaluation is time-consuming, resource-intensive and not reproducible in every environment, particularly for traits like disease resistance. The markers provided by the invention offer an effective alternative and therefore represent a significant advance in the art.

Phenotypic evaluation of large populations is time-consuming, resource-intensive and not reproducible in every environment. Marker-assisted selection offers a feasible alternative. Molecular assays designed to detect unique polymorphisms, such as SNPs, are versatile. However, they may fail to discriminate alleles within and among *Solanum* species in a single assay. Structural rearrangements of chromosomes such as deletions impair hybridization and extension of synthetically labeled oligonucleotides. In the case of duplication events, multiple copies are amplified in a single reaction without distinction. The development and validation of accurate and highly predictive markers are therefore essential for successful MAS breeding programs.

IV. MOLECULAR ASSISTED BREEDING TECHNIQUES

Genetic markers that can be used in the practice of the present invention include, but are not limited to, restriction fragment length polymorphisms (RFLPs), amplified fragment length polymorphisms (AFLPs), simple sequence repeats (SSRs), simple sequence length polymorphisms (SSLPs), single nucleotide polymorphisms (SNPs), insertion/deletion polymorphisms (Indels), variable number tandem repeats (VNTRs), and random amplified polymorphic DNA (RAPD), isozymes, and other markers known to those skilled in the art. Vegetable breeders use molecular markers to interrogate a crop's genome and classify material based on genetic, rather than phenotypic, differences. Advanced marker technologies are based on genome sequences, the nucleotide order of distinct, polymorphic genotypes within a species. Such platforms enable selection for horticultural traits with markers linked to favorable alleles, in addition to the organization of germplasm using markers randomly distributed throughout the genome. In the past, a priori knowledge of the genome lacked for major vegetable crops that now have been sequenced. Scientists exploited sequence homology, rather than known polymorphisms, to develop marker platforms. Man-made DNA molecules are used to prime replication of genome fragments when hybridized pair-wise in the presence of a DNA polymerase enzyme. This synthesis, regulated by thermal cycling conditions that control hybridization and replication of DNA strands in the polymerase chain reaction (PCR) to amplify DNA fragments of a length dependent on the distance between each primer pair. These fragments are then detected as markers and commonly known examples include AFLP and RAPD. A third technique, RFLP does not include a DNA amplification step. Amplified fragment length polymorphism (AFLP) technology reduces the complexity of the genome. First, through digestive enzymes cleaving DNA strands in a sequence-specific manner. Fragments are then selected for their size and finally replicated using selective oligonucleotides, each homologous to a subset of genome fragments. As a result, AFLP technology consistently amplifies DNA fragments across genotypes, experiments and laboratories.

Polymorphisms comprising as little as a single nucleotide change can be assayed in a number of ways. For example, detection can be made by electrophoretic techniques including a single strand conformational polymorphism (Orita et al., *Genomics* 8:271-278, 1989), denaturing gradient gel electrophoresis (Myers, EP 0273085), or cleavage fragment length polymorphisms (Life Technologies, Inc., Gaithersburg, Md.), but the widespread availability of DNA sequencing often makes it easier to simply sequence amplified products directly. Once the polymorphic sequence difference is known, rapid assays can be designed for progeny testing, typically involving some version of PCR amplification of specific alleles (PASA; Sommer et al., *Biotechniques* 12:82-87, 1992), or PCR amplification of multiple specific alleles (PAMSA; Dutton and Sommer, *Biotechniques* 11:700-702, 1991).

Polymorphic markers serve as useful tools for assaying plants for determining the degree of identity of lines or varieties (U.S. Pat. No. 6,207,367). These markers form the basis for determining associations with phenotypes and can be used to drive genetic gain. In certain embodiments of methods of the invention, polymorphic nucleic acids can be used to detect in a *Solanum lycopersicum* plant a genotype associated with disease resistance, identify a *Solanum lyco-*

*persicum* plant with a genotype associated with disease resistance, and to select a *Solanum lycopersicum* plant with a genotype associated with disease resistance. In certain embodiments of methods of the invention, polymorphic nucleic acids can be used to produce a *Solanum lycopersicum* plant that comprises in its genome an introgressed locus associated with disease resistance. In certain embodiments of the invention, polymorphic nucleic acids can be used to breed progeny *Solanum lycopersicum* plants comprising a locus associated with disease resistance.

Genetic markers may include "dominant" or "codominant" markers. "Codominant" markers reveal the presence of two or more alleles (two per diploid individual). "Dominant" markers reveal the presence of only a single allele. Markers are preferably inherited in codominant fashion so that the presence of both alleles at a diploid locus, or multiple alleles in triploid or tetraploid loci, are readily detectable, and they are free of environmental variation, i.e., their heritability is 1. A marker genotype typically comprises two marker alleles at each locus in a diploid organism. The marker allelic composition of each locus can be either homozygous or heterozygous. Homozygosity is a condition where both alleles at a locus are characterized by the same nucleotide sequence. Heterozygosity refers to different conditions of the allele at a locus.

Nucleic acid-based analyses for determining the presence or absence of the genetic polymorphism (i.e., for genotyping) can be used in breeding programs for identification, selection, introgression, and the like. A wide variety of genetic markers for the analysis of genetic polymorphisms are available and known to those of skill in the art. The analysis may be used to select for genes, portions of genes, QTL, alleles, or genomic regions that comprise or are linked to a genetic marker that is linked to or associated with disease resistance in *Solanum lycopersicum* plants.

As used herein, nucleic acid analysis methods include, but are not limited to, PCR-based detection methods (for example, TaqMan assays), microarray methods, mass spectrometry-based methods and/or nucleic acid sequencing methods, including whole genome sequencing. In certain embodiments, the detection of polymorphic sites in a sample of DNA, RNA, or cDNA may be facilitated through the use of nucleic acid amplification methods. Such methods specifically increase the concentration of polynucleotides that span the polymorphic site, or include that site and sequences located either distal or proximal to it. Such amplified molecules can be readily detected by gel electrophoresis, fluorescence detection methods, or other means.

One method of achieving such amplification employs the polymerase chain reaction (PCR) (Mullis et al., *Cold Spring Harbor Symp. Quant. Biol.* 51:263-273, 1986; European Patent 50,424; European Patent 84,796; European Patent 258,017; European Patent 237,362; European Patent 201,184; U.S. Pat. Nos. 4,683,202; 4,582,788; and 4,683,194), using primer pairs that are capable of hybridizing to the proximal sequences that define a polymorphism in its double-stranded form. Methods for typing DNA based on mass spectrometry can also be used. Such methods are disclosed in U.S. Pat. Nos. 6,613,509 and 6,503,710, and references found therein.

Polymorphisms in DNA sequences can be detected or typed by a variety of effective methods well known in the art including, but not limited to, those disclosed in U.S. Pat. Nos. 5,468,613; 5,217,863; 5,210,015; 5,876,930; 6,030,787; 6,004,744; 6,013,431; 5,595,890; 5,762,876; 5,945,283; 5,468,613; 6,090,558; 5,800,944; 5,616,464; 7,312,039; 7,238,476; 7,297,485; 7,282,355; 7,270,981 and 7,250,252 all of which are incorporated herein by reference in their entirety. However, the compositions and methods of the present invention can be used in conjunction with any polymorphism typing method to type polymorphisms in genomic DNA samples. These genomic DNA samples used include but are not limited to, genomic DNA isolated directly from a plant, cloned genomic DNA, or amplified genomic DNA.

For instance, polymorphisms in DNA sequences can be detected by hybridization to allele-specific oligonucleotide (ASO) probes as disclosed in U.S. Pat. Nos. 5,468,613 and 5,217,863. U.S. Pat. No. 5,468,613 discloses allele specific oligonucleotide hybridizations where single or multiple nucleotide variations in nucleic acid sequence can be detected in nucleic acids by a process in which the sequence containing the nucleotide variation is amplified, spotted on a membrane and treated with a labeled sequence-specific oligonucleotide probe.

Target nucleic acid sequence can also be detected by probe ligation methods, for example as disclosed in U.S. Pat. No. 5,800,944 where sequence of interest is amplified and hybridized to probes followed by ligation to detect a labeled part of the probe.

Microarrays can also be used for polymorphism detection, wherein oligonucleotide probe sets are assembled in an overlapping fashion to represent a single sequence such that a difference in the target sequence at one point would result in partial probe hybridization (Borevitz et al., *Genome Res.* 13:513-523, 2003; Cui et al., *Bioinformatics* 21:3852-3858, 2005). On any one microarray, it is expected there will be a plurality of target sequences, which may represent genes and/or noncoding regions wherein each target sequence is represented by a series of overlapping oligonucleotides, rather than by a single probe. This platform provides for high throughput screening of a plurality of polymorphisms. Typing of target sequences by microarray-based methods is disclosed in U.S. Pat. Nos. 6,799,122; 6,913,879; and 6,996,476.

Other methods for detecting SNPs and Indels include single base extension (SBE) methods. Examples of SBE methods include, but are not limited, to those disclosed in U.S. Pat. Nos. 6,004,744; 6,013,431; 5,595,890; 5,762,876; and 5,945,283.

In another method for detecting polymorphisms, SNPs and Indels can be detected by methods disclosed in U.S. Pat. Nos. 5,210,015; 5,876,930; and 6,030,787 in which an oligonucleotide probe having a 5' fluorescent reporter dye and a 3' quencher dye covalently linked to the 5' and 3' ends of the probe. When the probe is intact, the proximity of the reporter dye to the quencher dye results in the suppression of the reporter dye fluorescence, e.g. by Forster-type energy transfer. During PCR forward and reverse primers hybridize to a specific sequence of the target DNA flanking a polymorphism while the hybridization probe hybridizes to polymorphism-containing sequence within the amplified PCR product. In the subsequent PCR cycle DNA polymerase with 5'→3' exonuclease activity cleaves the probe and separates the reporter dye from the quencher dye resulting in increased fluorescence of the reporter.

In another embodiment, a locus or loci of interest can be directly sequenced using nucleic acid sequencing technologies. Methods for nucleic acid sequencing are known in the art and include technologies provided by 454 Life Sciences (Branford, Conn.), Agencourt Bioscience (Beverly, Mass.), Applied Biosystems (Foster City, Calif.), LI-COR Biosciences (Lincoln, Nebr.), NimbleGen Systems (Madison, Wis.), Illumina (San Diego, Calif.), and VisiGen Biotechnologies (Houston, Tex.). Such nucleic acid sequencing technologies comprise formats such as parallel bead arrays, sequencing by ligation, capillary electrophoresis, electronic microchips, "biochips," microarrays, parallel microchips, and single-molecule arrays.

V. DEFINITIONS

The following definitions are provided to better define the present invention and to guide those of ordinary skill in the art in the practice of the present invention. Unless otherwise noted, terms are to be understood according to conventional usage by those of ordinary skill in the relevant art.

As used herein, the term "plant" includes plant cells, plant protoplasts, plant cells of tissue culture from which *Solanum lycopersicum* plants can be regenerated, plant calli, plant clumps and plant cells that are intact in plants or parts of plants such as pollen, flowers, seeds, leaves, stems, and the like.

As used herein, the term "population" means a genetically heterogeneous collection of plants that share a common parental derivation.

As used herein, the terms "variety" and "cultivar" mean a group of similar plants that by their genetic pedigrees and performance can be identified from other varieties within the same species.

As used herein, an "allele" refers to one of two or more alternative forms of a genomic sequence at a given locus on a chromosome.

A "Quantitative Trait Locus (QTL)" is a chromosomal location that encodes for at least a first allele that affects the expressivity of a phenotype.

As used herein, a "marker" means a detectable characteristic that can be used to discriminate between organisms. Examples of such characteristics include, but are not limited to, genetic markers, biochemical markers, metabolites, morphological characteristics, and agronomic characteristics.

As used herein, the term "phenotype" means the detectable characteristics of a cell or organism that can be influenced by gene expression.

As used herein, the term "genotype" means the specific allelic makeup of a plant.

As used herein, "cultivated" or "elite" as used herein synonymously. A "cultivated line" or "elite line" refers to any line that has resulted from breeding and selection for superior agronomic performance. A "cultivated tomato plant" or "elite tomato plant" refers to a plant belonging to a cultivated tomato line. Numerous cultivated lines are available and known to those of skill in the art of tomato breeding. Exemplary cultivated lines are those of the species *Solanum lycopersicum*. A "cultivated tomato plant" may also refer to a grafted tomato plant, where the scion is from a cultivated species (a *Solanum lycopersicum* line) and the rootstock is from a wild tomato species (a line from *Solanum habrochaites, Solanum pimpinellifolium, Solanum peruvianum*, etc.). A "cultivated population" or "elite population" is an assortment of cultivated/elite individuals or lines that can be used to represent the state of the art in terms of agronomically superior genotypes of a given crop species, such as a *Solanum lycopersicum* line. Similarly, a cultivated/elite germplasm or strain of germplasm is an agronomically superior germplasm.

As used herein, the term "introgressed," when used in reference to a genetic locus, refers to a genetic locus that has been introduced into a new genetic background, such as through backcrossing. Introgression of a genetic locus can be achieved through plant breeding methods and/or by molecular genetic methods. Such molecular genetic methods include, but are not limited to, marker assisted selection, various plant transformation techniques and/or methods that provide for homologous recombination, non-homologous recombination, site-specific recombination, and/or genomic modifications that provide for locus substitution or locus conversion.

As used herein, the term "linked," when used in the context of nucleic acid markers and/or genomic regions, means that the markers and/or genomic regions are located on the same linkage group or chromosome such that they tend to segregate together at meiosis.

As used herein, "resistance locus" means a locus associated with resistance or tolerance to disease. For instance, a resistance locus according to the present invention may, in one embodiment, control resistance or susceptibility to black rot.

As used herein, "resistance allele" means the nucleic acid sequence associated with resistance or tolerance to disease.

As used herein "resistance" or "improved resistance" in a plant to disease conditions is an indication that the plant is less affected by disease conditions with respect to yield, survivability and/or other relevant agronomic measures, compared to a less resistant, more "susceptible" plant. Resistance is a relative term, indicating that a "resistant" plant survives and/or produces better yields in disease conditions compared to a different (less resistant) plant grown in similar disease conditions. As used in the art, disease "tolerance" is sometimes used interchangeably with disease "resistance." One of skill will appreciate that plant resistance to disease conditions varies widely, and can represent a spectrum of more-resistant or less-resistant phenotypes. However, by simple observation, one of skill can generally determine the relative resistance or susceptibility of different plants, plant lines or plant families under disease conditions, and furthermore, will also recognize the phenotypic gradations of "resistant."

The term "about" is used to indicate that a value includes the standard deviation of error for the device or method being employed to determine the value. The use of the term "or" in the claims is used to mean "and/or" unless explicitly indicated to refer to alternatives only or the alternatives are mutually exclusive, although the disclosure supports a definition that refers to only alternatives and to "and/or." When used in conjunction with the word "comprising" or other open language in the claims, the words "a" and "an" denote "one or more," unless specifically noted. The terms "comprise," "have" and "include" are open-ended linking verbs. Any forms or tenses of one or more of these verbs, such as "comprises," "comprising," "has," "having," "includes" and "including," are also open-ended. For example, any method that "comprises," "has" or "includes" one or more steps is not limited to possessing only those one or more steps and also covers other unlisted steps. Similarly, any plant that "comprises," "has" or "includes" one or more traits is not limited to possessing only those one or more traits and covers other unlisted traits.

VI. DEPOSIT INFORMATION

A deposit was made of at least 625 seeds of *Solanum pimpinellifolium* line LA1257, which comprises the increased disease resistance loci on chromosome 1 and chromosome 6, as described herein. The deposit was made with the American Type Culture Collection (ATCC), 10801 University Boulevard, Manassas, Va. 20110-2209 USA. The deposit is assigned ATCC Accession No. PTA-126291, and the date of deposit was Oct. 11, 2019. Access to the deposit will be available during the pendency of the application to persons entitled thereto upon request. The deposit will be maintained in the ATCC Depository, which is a public depository, for a period of 30 years, or 5 years after the most recent request, or for the enforceable life of the patent, whichever is longer, and will be replaced if nonviable during that period. Applicant does not waive any infringement of their rights granted under this patent or any other form of variety protection, including the Plant Variety Protection Act (7 U.S.C. 2321 et seq.).

Example 1

Identification of Resistance Source for Mi-1-breaking Root-Knot Nematodes

A seedling assay was used to screen for Mi-1-breaking nematodes resistant plants. Mi-1-breaking nematode isolates are defined, as the name suggests, as isolates that cause infectious disease in tomato plants that have Mi-1 resistance. As such any test for resistance to resistance breaking Mi-1 isolates should at least include two types of controls: a fully susceptible variety, e.g., GT, and a variety that has the Mi-1 gene, e.g., Nemato. Infectious nematode isolates from all over the world were used in the screen: two Mi-1-breaking isolates, one from Morocco (*Meloidogyne javanica*) and one non-breaking isolate (*Meloidogyne incognita*) from the Netherlands. The different tomato accessions were tested by infecting 2-3 week old seedlings with around 400 living nematodes. For such a disease screen, only seedlings with a properly developed root system were used. The plants were evaluated between 3 to 4 weeks post-infection when the negative control plants were starting to show symptoms. Resistance was determined by the number of galls found in the root system of the plant. In addition, each plant was given a nematode infection visual score using a 1-9 scale, where 1 equals no infection and 9 equals heavily infected roots (FIG. 1B). It was found that *Solanum pimpinellifolium* line LA1257, which can be obtained from the ATCC under Accession No. PTA-126291 and from the Tomato Genetic Resource Center in Davis, USA, was highly resistant against the *Meloidogyne javanica* isolate and intermediately resistant against the *Meloidogyne. incognita* isolate. The inventors thus concluded that *Solanum pimpinellifolium* line LA1257 could be used as a source for resistance against Mi-1-breaking RKN.

Example 2

Figure 2:
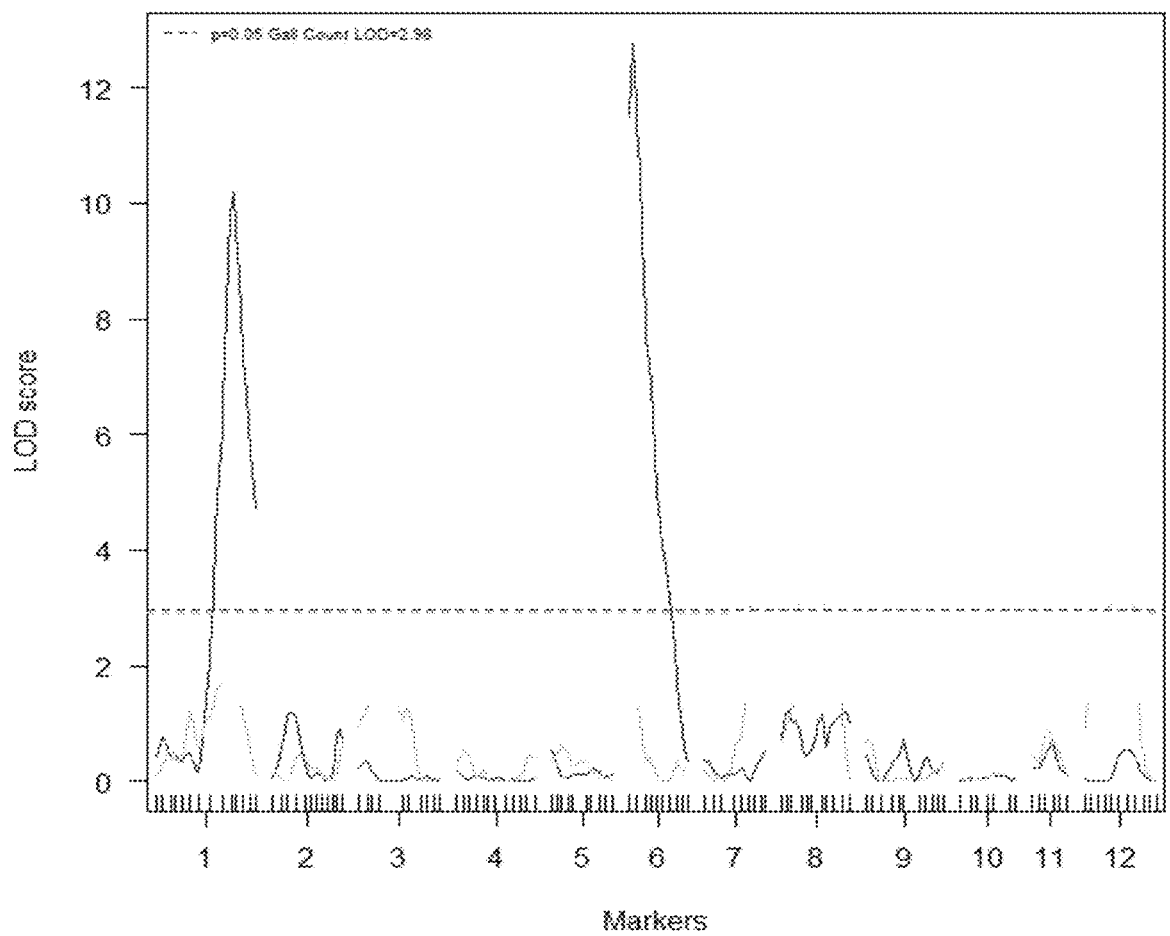
FIG. 2: Shows LOD score peaks produced by mapping of the root-knot nematode (RKN) resistance QTLs identified in the *Solanum pimpinellifolium* line LA1257. In total, two significant peaks were identified on chromosomes 1 and 6. The dashed line indicates the significance threshold for the LOD scores (i.e., peaks extending above this LOD-value are considered to be significant).

Mapping of Mi-1-breaking RKN Resistance QTLs and Identification of Trait-Linked Markers The genetics behind the Mi-1-breaking RKN resistance of *Solanum pimpinellifolium* line LA1257 was determined by developing a mapping population using LA1257 with susceptible control line GT. Pollen of LA1257 was used to fertilize flowers of GT. The $F_1$ of this cross was self-pollinated to generate $F_2$ seed. $F_2$ plants were then self-fertilized to generate F2:3 populations consisting of 300 families. The Mi-1-breaking RKN resistance phenotype was determined in the same bioassay as described above using the *Meloidogyne javanica* isolate from Morocco. For each family and parent, the least square mean (LSM) was determined for the number of galls in the root system. There was significant variation in resistance levels among the families, indicating that the Mi-1-breaking RKN resistance was heritable and transferable to *Solanum lycopersicum* plants. Subsequently, plants of lines LA1257 and GT were fingerprinted and polymorphic SNPs were identified. Those SNPs were used to map the resistance QTLs using 200 of the 300 original families. QTL analysis revealed two QTLs that, together, explained about 70% of the phenotypic variation. One QTL was located on chromosome 1 and spans a 30 cM region. The other QTL was identified on chromosome 6 and spans a 16 cM region (FIG. 2).

Example 3

Fine-Mapping of the Mi-1-Breaking RKN Resistance Trait-Linked Intervals

For fine-mapping, a new population was developed using a $F_3$ line from the LA1257×GT cross that was homozygous for both resistance regions. The susceptible recurrent parent was an indeterminate line that produces round tomato fruit. This population was developed to a $BC_4F_2$ generation where two lines were selected that contained both loci in a heterozygous state. These family were mined for recombinants in the nematode resistance regions on chromosome 1 and chromosome 6. Heterozygous recombinants were fixed in the next generation. For optimal detection of nematode resistance levels, plants need to be at least heterozygous for the locus on chromosome 1 and for the locus on chromosome 6. Therefore, during the mining for recombinants, only plants were selected that were fixed for the locus in which there was no recombination event detected. In total, 94 recombinant lines representing 58 unique genotypes were picked and phenotyped for nematode resistance. These lines were genotyped and a QTL analysis was performed. The locus on chromosome 1 was fine-mapped to an approximately 0.4 cM region between markers M2 (SEQ ID NO:1) and M3 (SEQ ID NO:8). In addition, interstitial markers M11 (SEQ ID NO:6), M12 (SEQ ID NO:7), and M13 (SEQ ID NO:8) were developed to select for the nematode resistance locus on chromosome 1. The locus on chromosome 6 was fine-mapped to an approximately 0.3 cM region between markers M6 (SEQ ID NO:10) and M10 (SEQ ID NO:26). Interstitial markers M7 (SEQ ID NO:11), M8 (SEQ ID NO:16), and M9 (SEQ ID NO:21) were developed to select the nematode resistance locus on chromosome 6. Table 1 shows markers associated with the resistance QTLs on chromosomes 1 and 6 that can be used for tracking and selection of the loci.

TABLE 1

Markers to track Solanum pimpinellifolium-derived resistance to Mi-1-breaking RKN on chromosomes 1 and 6.

| Marker | Chr | Favorable Allele | SNP change | SNP position in marker (bp) | Position (cM) | SNP Position in Public Genome (bp) | Marker Sequence (SEQ ID NO) | Fwd Primer (SEQ ID NO) | Rev Primer (SEQ ID NO) | Probe 1 (SEQ ID NO) | Probe 2 (SEQ ID NO) |
|---|---|---|---|---|---|---|---|---|---|---|---|
| M2 | 1 | C | A/C | 195 | 113.00 | 82,703,136 | 1 | 2 | 3 | 4 | 5 |
| M11 | 1 | G | C/G | 151 | 113.03 | 82,711,231 | 6 | n/a | n/a | n/a | n/a |
| M12 | 1 | C | T/C | 151 | 114.04 | 82,992,118 | 7 | n/a | n/a | n/a | n/a |
| M13 | 1 | T | C/T | 151 | 114.92 | 83,278,437 | 8 | n/a | n/a | n/a | n/a |
| M3 | 1 | G | G/T | 310 | 114.99 | 83,446,695 | 9 | n/a | n/a | n/a | n/a |
| M6 | 6 | G | C/G | 451 | 3.38 | 2,076,193 | 10 | n/a | n/a | n/a | n/a |
| M7 | 6 | A | G/A | 151 | 3.61 | 2,519,127 | 11 | 12 | 13 | 14 | 15 |
| M8 | 6 | C | C/A | 603 | 3.66 | 2,633,793 | 16 | 17 | 18 | 19 | 20 |
| M9 | 6 | A | G/A | 338 | 3.66 | 2,381,634 | 21 | 22 | 23 | 24 | 25 |
| M10 | 6 | G | A/G | 171 | 3.66 | 2,842,551 | 26 | n/a | n/a | n/a | n/a |

To validate the efficacy of the two Mi-1-breaking RKN resistance loci across tomato genotypes, the resistance alleles were introgressed into tomato lines having varying genetic backgrounds. These tomato lines include those used for the production of fresh market fruit and tomato rootstock lines. It was found that lines where both Mi-1-breaking RKN resistance QTLs were present demonstrated the highest level of resistance. Both heterozygously deployed resistance QTLs and homozygously deployed resistance QTLs provide a significant increase in nematode resistance levels in all the backgrounds that were tested. In some backgrounds, a homozygously deployed Mi-1-breaking RKN resistance QTL on chromosome 6 in combination with a heterozygous or homozygous Mi-1-breaking RKN resistance QTL on chromosome 1 resulted in the highest level of resistance. However, most breeders will choose to deploy the locus on chromosome 6 heterozygously in combination with the nematode resistance locus Mi-1 from *Solanum peruvianum*, as the two loci are located in the same genomic region and together provide resistance to broad range of nematodes.

Example 4

Newly Identified Mi-1-Breaking RKN Resistance QTLs Improve Root Vigor

In an adult plant assay using material in the GT background, lines were evaluated for root development and gall infection, both on a 1-9 scale (FIGS. 1A and 1B, respectively). Table 2 shows the quantitative data obtained from seedling and adult plant assays. The results of the assays demonstrate that plants comprising both the Mi-1-breaking RKN resistance QTL on chromosome 1 and the Mi-1-breaking RKN resistance QTL on chromosome 6, wherein at least one locus is present as a homozygote, significantly improves root development in the presence and in the absence of nematodes. The results also demonstrate that presence of both Mi-1-breaking RKN resistance QTLs in a plant increases the plant's resistance to RKN when compared to plants of the same genetic background that have either one or none of the Mi-1-breaking RKN resistance QTLs present. Table 2 also shows the mean level of root development for the same plants in the presence (RKN infection) and absence (water) of RKN.

TABLE 2

Seedling and adult plant assays for RKN resistance and root development.

| | | | Seedling assay | | | | Adult Plant Assay | | | |
|---|---|---|---|---|---|---|---|---|---|---|
| | | | Rough Mapping | | | | QTL Validation | | | |
| | Genotype Chr 1 | Chr 6 | MS Group | Gall Count LSM | MS Group | RKN Infection LSM | MS Group | RKN Infection LSM | MS Group | Root vigor LSM |
| S Parent | Null | Null | AB | 101.3 | A | 7.90 | A | 9.00 | A | 9.00 |
| | Het | Null | A | 99.7 | B | 6.15 | | | | |
| | Null | Null | AB | 94.2 | B | 6.40 | A | 8.83 | AB | 8.67 |
| | Null | Het | BC | 84.5 | B | 6.22 | | | | |
| | Hom | Null | CD | 75.4 | B | 6.33 | A | 8.83 | AB | 8.00 |
| | Null | Hom | D | 63.8 | B | 5.40 | A | 8.85 | AB | 8.25 |
| | Het | Het | E | 48.5 | C | 2.98 | B | 5.81 | C | 4.00 |
| | Het | Hom | F | 33.4 | CD | 2.33 | C | 2.98 | C | 4.20 |
| | Hom | Het | F | 30.3 | CD | 2.61 | B | 6.67 | C | 4.00 |
| R parent | Hom | Hom | FG | 16.5 | E | 1.00 | | | | |
| | Hom | Hom | G | 14.1 | DE | 1.75 | | | | |

All of the compositions and/or methods disclosed and claimed herein can be made and executed without undue experimentation in light of the present disclosure. While the compositions and methods of this invention have been described in terms of preferred embodiments, it will be apparent to those of skill in the art that variations may be applied to the compositions and/or methods and in the steps or in the sequence of steps of the method described herein without departing from the concept, spirit and scope of the invention. More specifically, it will be apparent that certain agents that are both chemically and physiologically related may be substituted for the agents described herein while the same or similar results would be achieved. All such similar substitutes and modifications apparent to those skilled in the art are deemed to be within the spirit, scope and concept of the invention as defined by the appended claims.

What is claimed is:

1. A cultivated tomato plant comprising a recombinant chromosomal segment on chromosome 1 from *Solanum pimpinellifolium* on chromosome 1, wherein said recombinant chromosomal segment comprises an allele that confers increased resistance to Mi-1 resistance-breaking root-knot nematode species relative to a plant lacking said recombinant chromosomal segment, wherein said Mi-1 resistance-breaking root-knot nematode species resistance allele is located between 82,703,136 bp and 83,446,695 bp on chromosome 1 of the public tomato genome sequence SL3.0, and wherein said recombinant chromosomal segment comprises a marker locus selected from the group consisting of marker locus M2 (SEQ ID NO:1), marker locus M11 (SEQ ID NO:6), marker locus M12 (SEQ ID NO:7), marker locus M13 (SEQ ID NO:8), and marker locus M3 (SEQ ID NO:9).

2. The plant of claim 1, wherein:
   a) said resistance comprises resistance to nematode species *Meloidogyne javanica, Meloidogyne incognita,* or *Meloidogyne enterolobii;*
   b) the plant is homozygous for said recombinant chromosomal segment; or
   c) a sample of seed comprising said Mi-1 resistance-breaking root-knot nematode species resistance allele was deposited under ATCC Accession Number PTA-126291.

3. The plant of claim 2, wherein said resistance comprises resistance to nematode species *Meloidogyne javanica*.

4. A seed that produces the plant of claim 1.

5. A plant part of the plant of claim 1.

6. The plant part of claim 5, wherein the plant part is a cell, a seed, a root, a stem, a leaf, a fruit, a flower, or pollen.

7. The cultivated tomato plant of claim 1, further comprising a recombinant chromosomal segment on chromosome 6 from *Solanum pimpinellifolium* on chromosome 6, wherein said recombinant chromosomal segment on chromosome 6 comprise an allele that confers further increased resistance to Mi-1 resistance-breaking root-knot nematode species relative to a plant lacking said first or second recombinant chromosomal segment, and wherein said recombinant chromosomal segments on chromosomes 1 and 6 confer increased root vigor relative to a plant lacking said recombinant chromosomal segments.

8. The plant of claim 7, wherein said plant is homozygous for said first or second recombinant chromosomal segment on chromosome 1 or chromosome 6.

9. A method for producing a cultivated tomato plant with improved resistance to Mi-1 resistance-breaking root-knot nematode species, comprising introgressing into said plant a Mi-1 resistance-breaking root-knot nematode species resistance allele from chromosome 1 of *Solanum pimpinellifolium* within a recombinant chromosomal segment flanked in the genome of said plant by marker locus M2 (SEQ ID NO:1) and marker locus M3 (SEQ ID NO:9) on chromosome 1, wherein said introgressed Mi-1 resistance-breaking root-knot nematode species resistance allele confers to said plant resistance to Mi-1 resistance-breaking root-knot nematode species relative to a plant lacking said allele.

10. The method of claim 9, wherein said introgressing comprises:
   a) crossing a plant comprising said recombinant chromosomal segment with itself or with a second cultivated tomato plant of a different genotype to produce one or more progeny plants; and
   b) selecting a progeny plant comprising said recombinant chromosomal segment.

11. The method of claim 10, wherein selecting a progeny plant comprises detecting nucleic acids comprising marker locus M2 (SEQ ID NO:1), marker locus M11 (SEQ ID NO:6), marker locus M12 (SEQ ID NO:7), marker locus M13 (SEQ ID NO:8), and marker locus M3 (SEQ ID NO:9) on chromosome 1.

12. The method of claim 9, wherein:
a) said resistance comprises resistance to nematode species *Meloidogyne javanica, Meloidogyne incognita*, or *Meloidogyne enterolobii*;
b) said introgressing comprises backcrossing, marker-assisted selection, or assaying for said resistance to Mi-1 resistance-breaking root-knot nematode species; or
c) said plant further comprises a second introgressed Mi-1 resistance-breaking root-knot nematode species resistance allele from *Solanum pimpinellifolium* within a recombinant chromosomal segment flanked in the genome of said plant by marker locus M2 (SEQ ID NO:1) and marker locus M3 (SEQ ID NO:9) on chromosome 1.

13. The method of claim 12, wherein said resistance comprises resistance to nematode species *Meloidogyne javanica*.

14. The method of claim 10, wherein the progeny plant is an $F_2$-$F_6$ progeny plant.

15. A cultivated tomato plant produced by the method of claim 9, wherein said Mi-1 resistance-breaking root-knot nematode species resistance allele is located between 82,703,136 bp and 83,446,695 bp on chromosome 1 of the public tomato genome sequence SL3.0.

16. A method of selecting a cultivated tomato plant exhibiting resistance to Mi-1 resistance-breaking root-knot nematode species, comprising:

a) crossing the cultivated tomato plant of claim 1 with itself or with a second cultivated tomato plant of a different genotype to produce one or more progeny plants; and
b) selecting a progeny plant comprising said Mi-1 resistance-breaking root-knot nematode species resistance allele.

17. The method of claim 16, wherein selecting said progeny plant comprises detecting a marker locus genetically linked to said Mi-1 resistance-breaking root-knot nematode species resistance allele.

18. The method of claim 17, wherein selecting said progeny plant comprises detecting a marker locus within or genetically linked to a chromosomal segment flanked in the genome of said plant by marker locus M2 (SEQ ID NO:1) and marker locus M3 (SEQ ID NO:9) on chromosome 1.

19. The method of claim 17, wherein selecting said progeny plant comprises detecting nucleic acids comprising marker locus M2 (SEQ ID NO:1), marker locus M11 (SEQ ID NO:6), marker locus M12 (SEQ ID NO:7), marker locus M13 (SEQ ID NO:8), and marker locus M3 (SEQ ID NO:9) on chromosome 1.

20. The method of claim 16, wherein:
a) said progeny plant is an $F_2$-$F_6$ progeny plant; or
b) producing said progeny plant comprises backcrossing.

* * * * *

UNITED STATES PATENT AND TRADEMARK OFFICE
CERTIFICATE OF CORRECTION

PATENT NO. : 11,608,507 B2  
APPLICATION NO. : 17/095382  
DATED : March 21, 2023  
INVENTOR(S) : Kelli M. Durham et al.

Page 1 of 1

It is certified that error appears in the above-identified patent and that said Letters Patent is hereby corrected as shown below:

In the Claims

In Column 34, Line 32, delete "species relative to a plant lacking said first or second" and insert --species relative to a plant lacking said--

In Column 34, Line 38, delete "for said first or second recombinant chromosomal segment" and insert --for said recombinant chromosomal segment--

Signed and Sealed this  
Twenty-first Day of November, 2023

Katherine Kelly Vidal  
*Director of the United States Patent and Trademark Office*

SEQUENCE LISTING

```
<160> NUMBER OF SEQ ID NOS: 26

<210> SEQ ID NO 1
<211> LENGTH: 384
<212> TYPE: DNA
<213> ORGANISM: Solanum pimpinellifolium

<400> SEQUENCE: 1
taaacaccaa actttatgct tttttatcct taatgcgatc aactgctaca attccagaaa      60
accacttcca tagtctaggg tccatatagt agttaaacat aactacatga tgtgtctctg     120
tgtccatata gagcctatat ctagtatcag ctactctatc ctttccaatt tataccgtgc     180
tgtttgattt cgtamatgtc tttccaattt ttatgatggt gctcaatttt gacatagttt     240
aagatattca tttttgtctt atgtattata tcagtttgta acggaaaaaa gagtgaatta     300
atggttgaaa agttagcttg atagagaaaa agtcgcttga gagttaaata tttatataat     360
taaatggatt tgaattctta gagt                                            384

<210> SEQ ID NO 2
<211> LENGTH: 28
<212> TYPE: DNA
<213> ORGANISM: Artificial Sequence
<220> FEATURE:
<223> OTHER INFORMATION: Primer

<400> SEQUENCE: 2
caattccaga aaaccacttc catagtct                                         28

<210> SEQ ID NO 3
<211> LENGTH: 35
<212> TYPE: DNA
<213> ORGANISM: Artificial Sequence
<220> FEATURE:
<223> OTHER INFORMATION: Primer

<400> SEQUENCE: 3
tcactctttt ttccgttaca aactgatata ataca                                 35

<210> SEQ ID NO 4
<211> LENGTH: 19
<212> TYPE: DNA
<213> ORGANISM: Artificial Sequence
<220> FEATURE:
<223> OTHER INFORMATION: Probe

<400> SEQUENCE: 4
tttgatttcg taaatgtct                                                   19

<210> SEQ ID NO 5
<211> LENGTH: 19
<212> TYPE: DNA
<213> ORGANISM: Artificial Sequence
<220> FEATURE:
<223> OTHER INFORMATION: Probe
```

<400> SEQUENCE: 5
tttgatttcg tacatgtct                                                    19

<210> SEQ ID NO 6
<211> LENGTH: 301
<212> TYPE: DNA
<213> ORGANISM: Solanum pimpinellifolium
<220> FEATURE:
<221> NAME/KEY: misc_feature
<222> LOCATION: (6)..(6)
<223> OTHER INFORMATION: n is a, c, g, or t
<220> FEATURE:
<221> NAME/KEY: misc_feature
<222> LOCATION: (180)..(180)
<223> OTHER INFORMATION: n is a, c, g, or t
<220> FEATURE:
<221> NAME/KEY: misc_feature
<222> LOCATION: (182)..(182)
<223> OTHER INFORMATION: n is a, c, g, or t
<220> FEATURE:
<221> NAME/KEY: misc_feature
<222> LOCATION: (225)..(225)
<223> OTHER INFORMATION: n is a, c, g, or t
<220> FEATURE:
<221> NAME/KEY: misc_feature
<222> LOCATION: (276)..(276)
<223> OTHER INFORMATION: n is a, c, g, or t

<400> SEQUENCE: 6
aatccngtta gaggagaagg agcagttatt ggatgtgaat tataagcttt atacattgca        60
cttttgcatg aactcccttc ttctcctgat tgcgatccac aaccttcctt gtcaacatga       120
tggaaggaac ctgattgact gctgttatct scattcttttt tccccattcc aagatgaacn     180
anaaccttat ctgattcttt atcactggtt ttgtcatgaa tggtnagaag aattccgtct       240
cgtggagaaa aatcatttgt tgatacttgc tcaacncgaa cttctttaat ttccttagaa       300
a                                                                        301

<210> SEQ ID NO 7
<211> LENGTH: 301
<212> TYPE: DNA
<213> ORGANISM: Solanum pimpinellifolium
<220> FEATURE:
<221> NAME/KEY: misc_feature
<222> LOCATION: (173)..(173)
<223> OTHER INFORMATION: n is a, c, g, or t
<220> FEATURE:
<221> NAME/KEY: misc_feature
<222> LOCATION: (252)..(253)
<223> OTHER INFORMATION: n is a, c, g, or t

<400> SEQUENCE: 7
actaacaaga aattcatatg ttactcacag gggtctaaat ttatgatttg gtcttgtggt        60
gtcccaaaaa gtggagcaaa aaacaaagag aactttttt ccaaacacaa agcaaaagta       120
tgtttcaaat taagattaag aatccaagtg ytgatatatt agtgccttct ttnaaaaaac      180
tcaccacact gcttttttca ggcatcttac cctcttactt tattgcaaga aacctttccc       240
ctaatgtatt tnnaaaatca ccaagcatgg tactagctcc aaattttaac tgacatttcc       300
a                                                                        301

<210> SEQ ID NO 8
<211> LENGTH: 301
<212> TYPE: DNA
<213> ORGANISM: Solanum pimpinellifolium
<220> FEATURE:
<221> NAME/KEY: misc_feature

```
<222> LOCATION: (32)..(32)
<223> OTHER INFORMATION: n is a, c, g, or t
<220> FEATURE:
<221> NAME/KEY: misc_feature
<222> LOCATION: (44)..(44)
<223> OTHER INFORMATION: n is a, c, g, or t
<220> FEATURE:
<221> NAME/KEY: misc_feature
<222> LOCATION: (222)..(222)
<223> OTHER INFORMATION: n is a, c, g, or t
<220> FEATURE:
<221> NAME/KEY: misc_feature
<222> LOCATION: (279)..(279)
<223> OTHER INFORMATION: n is a, c, g, or t
<220> FEATURE:
<221> NAME/KEY: misc_feature
<222> LOCATION: (298)..(298)
<223> OTHER INFORMATION: n is a, c, g, or t

<400> SEQUENCE: 8 acttttgtg  gcttgcttta  gatgtagatg  anctctttct  tgcngagaga  ttttgaatcc      60
acagaaagaa  tcaataattt  aaaattgttc  agatactcta  acttgtcagg  aggttgcaac     120
catctgagaa  gtgtaatgta  tccctaattc  ygaaaactag  aaagacagac  actgcttagt     180
ggttgagcat  cttattctta  tttatcaata  tgtaacaact  gntagtagat  tatatttgca     240
atattctcac  gtatctttat  tatatatgga  gtcttactnt  tagttttaac  tcaattgntt     300
g                                                                         301

<210> SEQ ID NO 9
<211> LENGTH: 954
<212> TYPE: DNA
<213> ORGANISM: Solanum pimpinellifolium
<220> FEATURE:
<221> NAME/KEY: misc_feature
<222> LOCATION: (655)..(655)
<223> OTHER INFORMATION: n is a, c, g, or t
<220> FEATURE:
<221> NAME/KEY: misc_feature
<222> LOCATION: (953)..(954)
<223> OTHER INFORMATION: n is a, c, g, or t

<400> SEQUENCE: 9
tgagaaaggc  agcttttgaa  tgtgtagaca  cattgctaga  cacttgtctt  gatcaagtga      60
atccctcatc  tttcattgtc  ccatatcttc  aatctggttt  ggatggtaag  ttgatagctt     120
gtgatagacc  cgattcttct  attgttatct  ctatttttcc  aaatgtggtg  ttctgattct     180
tgatttgatt  ttattgatgt  ctgcaaattc  tatttttttg  gggatgggtg  tggccgtgtg     240
gtagcatcat  tggacatgtc  actgcgctca  catgcaatta  ttttactgct  gaactgaatc     300
ttttgcctcg  tctcccagat  cattatgatg  ttaaaatgcc  atgccacctt  atcctttcta     360
aacttgctga  taagtgtcct  tcagcggtat  tagcaggtat  agtctttttg  ctgctctttt     420
tctccttcta  atgaaccagt  ttgttatgtt  tacaatacat  tgcttttgca  gttctggact     480
ctttggtgga  tcctctgcag  aaaacaataa  atttcagacc  aaaacaggat  gctgtcaagc     540
aagaggttga  tcgcaatgaa  gacatgattc  gaagtgccct  tcgggcaatt  gcagccttaa     600
atcgtatcag  gtaagtcttt  ttttagtgtc  cccttgaaat  gattgtgctt  ttgtngacat     660
gtgtcttgaa  tcaataattt  aggggatga  ccttctctta  tccttttcgt  attttttcttg     720 ttctttctgt  gaaatggaa  gatttctatt  tcttttccag  tgtagcatat  ttcagatttt     780
tcataccaaa  atgaagttat  gagtcatcag  ctcatctact  gctactttg  attaggactg     840 cctttagggc  aatatacaag  tgttataaac  taagctcgat  atccatgtgt  gaaaaggaaa     900
```

```
atattcttgt tgcaatttga tacctctgtt tcctttcctc tcttctttt  ctnn         954
```

```
<210> SEQ ID NO 10
<211> LENGTH: 1101
<212> TYPE: DNA
<213> ORGANISM: Solanum pimpinellifolium
<220> FEATURE:
<221> NAME/KEY: misc_feature
<222> LOCATION: (1098)..(1098)
<223> OTHER INFORMATION: n is a, c, g, or t

<400> SEQUENCE: 10
```

```
aagactgaaa gcattgcaac aacaacagca gcaaaacaca gtgtaataca actagcgggg    60
tctagagagg atcgagtgta tgcaagacct taaccgtatc ttcgaaggta gagaagctgt   120
tacagataga ccctcggcca gaacaaaagc attgtaggga cagaactaac ttaaaactaa   180
agtaaagatg caagaaaagt attcataaaa tgagcaaaaa ttgctgagaa tacattgtct   240
tgggtcatct ttcaccataa aaataagtt cattaacagt attcacctac gaggaaaagt    300
gcctttgcat ttataaatta cttaccacac tgtacaacga gatgaaataa ataggatgcc   360
aaatgaatgg agagaacaat ttaaaggaga ctgacttcta gcttcagata attcaagctt   420
tctcctccta tgttacttgt tgagtaaccc saagaaaatc attgaaacta cgaacctaag   480
catgaagagc atctgaactt gagagtttgt acttctagtt caaatttaac caattattat   540
gaacactcct acccaattt tctcaaactt ttctagttaa ttatgctcgt ctatgcagag    600
cgctactcca acagaggcta gtaggcaaaa atagaaaaaa acatcaaaag aattggttca   660
aaaagagggg ggttcagtaa tttgacaaac aatacatgac tgtcctcaat gattgttcaa   720
ctctaaaata atatcattta tttatgctt caattgagga gaaagtaagg ccagtctatt    780
aaagaattca gaccactatt tcaggacatt attgaagttc aatttatgga aattgcaatg   840
aaatgaatat aacttccaat ttcaaagccg cgatatttat acaaaagtaa gttcatccta   900
agaaatgaag acattccaat aaaacataaa aatatgcatc tatagattga tgcaattaga   960
aatttctatt ggtcaatatg tatgtgcgag ttacatttta aaaagtcaaa gctcaatatc  1020
attgtgtaat ttatccaacc attgacgaaa ttgagagtta gagaaaaacg ataccttcag  1080
gcaactatag tatttccnttt t                                           1101
```

```
<210> SEQ ID NO 11
<211> LENGTH: 301
<212> TYPE: DNA
<213> ORGANISM: Solanum pimpinellifolium
<220> FEATURE:
<221> NAME/KEY: misc_feature
<222> LOCATION: (38)..(38)
<223> OTHER INFORMATION: n is a, c, g, or t
<220> FEATURE:
<221> NAME/KEY: misc_feature
<222> LOCATION: (73)..(73)
<223> OTHER INFORMATION: n is a, c, g, or t
<220> FEATURE:
<221> NAME/KEY: misc_feature
<222> LOCATION: (159)..(159)
<223> OTHER INFORMATION: n is a, c, g, or t
<220> FEATURE:
<221> NAME/KEY: misc_feature
<222> LOCATION: (178)..(178)
<223> OTHER INFORMATION: n is a, c, g, or t
<220> FEATURE:
<221> NAME/KEY: misc_feature
<222> LOCATION: (226)..(226)
<223> OTHER INFORMATION: n is a, c, g, or t
<220> FEATURE:
<221> NAME/KEY: misc_feature
```

```
<222> LOCATION: (242)..(242)
<223> OTHER INFORMATION: n is a, c, g, or t
<220> FEATURE:
<221> NAME/KEY: misc_feature
<222> LOCATION: (272)..(272)
<223> OTHER INFORMATION: n is a, c, g, or t
<220> FEATURE:
<221> NAME/KEY: misc_feature
<222> LOCATION: (275)..(275)
<223> OTHER INFORMATION: n is a, c, g, or t
<220> FEATURE:
<221> NAME/KEY: misc_feature
<222> LOCATION: (289)..(289)
<223> OTHER INFORMATION: n is a, c, g, or t

<400> SEQUENCE: 11
attttgaaat cgaaggacta taatcaacgt atccttgngg agtcaatctt tttacctcat      60
tatcgccctc gancgtacta gtgcagtaaa gagcagagga gcttgtgaaa atcttttcag    120
aatgttgatg agctgagatg taatagaggc rattattang aagaattgga cgatcganaa    180
ataaggtatt gattgaaata ggaattagtt caattcctga atgacnacga ctcaagtgaa    240
tncgaggagc acctgatctt tcagagacga anacnagtgt ctggtcttng tcaatgaatt    300
g                                                                    301

<210> SEQ ID NO 12
<211> LENGTH: 26
<212> TYPE: DNA
<213> ORGANISM: Artificial Sequence
<220> FEATURE:
<223> OTHER INFORMATION: Primer

<400> SEQUENCE: 12
gcagaggagc ttgtgaaaat cttttc                                          26

<210> SEQ ID NO 13
<211> LENGTH: 35
<212> TYPE: DNA
<213> ORGANISM: Artificial Sequence
<220> FEATURE:
<223> OTHER INFORMATION: Primer

<400> SEQUENCE: 13
cattcaggaa ttgaactaat tcctatttca atcaa                                35

<210> SEQ ID NO 14
<211> LENGTH: 20
<212> TYPE: DNA
<213> ORGANISM: Artificial Sequence
<220> FEATURE:
<223> OTHER INFORMATION: Probe

<400> SEQUENCE: 14
atgtaataga ggcgattatt                                                 20

<210> SEQ ID NO 15
<211> LENGTH: 19
<212> TYPE: DNA
<213> ORGANISM: Artificial Sequence
<220> FEATURE:
<223> OTHER INFORMATION: Probe

<400> SEQUENCE: 15
tgtaatagag gcaattatt                                                  19

<210> SEQ ID NO 16
```

<211> LENGTH: 914
<212> TYPE: DNA
<213> ORGANISM: Solanum pimpinellifolium
<220> FEATURE:
<221> NAME/KEY: misc_feature
<222> LOCATION: (25)..(25)
<223> OTHER INFORMATION: n is a, c, g, or t
<220> FEATURE:
<221> NAME/KEY: misc_feature
<222> LOCATION: (66)..(66)
<223> OTHER INFORMATION: n is a, c, g, or t
<220> FEATURE:
<221> NAME/KEY: misc_feature
<222> LOCATION: (87)..(87)
<223> OTHER INFORMATION: n is a, c, g, or t
<220> FEATURE:
<221> NAME/KEY: misc_feature
<222> LOCATION: (118)..(118)
<223> OTHER INFORMATION: n is a, c, g, or t
<220> FEATURE:
<221> NAME/KEY: misc_feature
<222> LOCATION: (154)..(154)
<223> OTHER INFORMATION: n is a, c, g, or t
<220> FEATURE:
<221> NAME/KEY: misc_feature
<222> LOCATION: (196)..(196)
<223> OTHER INFORMATION: n is a, c, g, or t
<220> FEATURE:
<221> NAME/KEY: misc_feature
<222> LOCATION: (289)..(289)
<223> OTHER INFORMATION: n is a, c, g, or t
<220> FEATURE:
<221> NAME/KEY: misc_feature
<222> LOCATION: (333)..(333)
<223> OTHER INFORMATION: n is a, c, g, or t
<220> FEATURE:
<221> NAME/KEY: misc_feature
<222> LOCATION: (543)..(543)
<223> OTHER INFORMATION: n is a, c, g, or t
<220> FEATURE:
<221> NAME/KEY: misc_feature
<222> LOCATION: (576)..(576)
<223> OTHER INFORMATION: n is a, c, g, or t
<220> FEATURE:
<221> NAME/KEY: misc_feature
<222> LOCATION: (754)..(754)
<223> OTHER INFORMATION: n is a, c, g, or t
<220> FEATURE:
<221> NAME/KEY: misc_feature
<222> LOCATION: (771)..(771)
<223> OTHER INFORMATION: n is a, c, g, or t
<220> FEATURE:
<221> NAME/KEY: misc_feature
<222> LOCATION: (813)..(813)
<223> OTHER INFORMATION: n is a, c, g, or t
<220> FEATURE:
<221> NAME/KEY: misc_feature
<222> LOCATION: (882)..(882)
<223> OTHER INFORMATION: n is a, c, g, or t
<220> FEATURE:
<221> NAME/KEY: misc_feature
<222> LOCATION: (914)..(914)
<223> OTHER INFORMATION: n is a, c, g, or t

<400> SEQUENCE: 16

```
gacacggacc cactattctg aaacngatgg tcattctttc tctccttatc ggagccttgg      60 tctganttte cagtcttgca agcaaantga ctagcttgac gtaagggatc tgcacttnca     120
tcggtatcct gttgagttgc ataaccagaa accntggact ttgctttgac ttttttacct    180
gattcacgat gaacancttt ctcctctaat tcagcttcag ataatagatc ataactcttg    240
ccattgcagg cattatcctt cttaaccata ctggatttat tggagaacnc atcattttca    300
ccatcagaag acctcttggg actagaagtg ggnaaggctg aagagggagc aacagaaggt    360
cgcgaattgc atagatcctt ttgtgaagaa tctgcagctt taacactcaa caaagataga    420
```

```
gtactatcca gatcttgccc agcctgctgt tcctttttaa cttgacctgt tccagcacta    480
cctttgcttg cactagtgtc cttccggtca gacaaggaga cccttgctac cttttccttc    540
ctngagatgt catcacatat tttttccata gaatcntggg gattacatgt caaggaatct    600
cgmagttctc tccctttctt cttaatcgga gaatcattat tgtcacactt cccttatgc     660 gttgacacat cggaaatata agcttctggg ttctttgctg aaaccaagtc tttctttgaa    720
tcatcctctg agtccctgtt cttacatttg tcangaatca tctctggcat nttactgctt    780
gaactccatc tagactttc aacaacaggg canaaggtct ggttctcgtc atcgagtgca     840
tcatcttgta taattttttt ggaagataca tctgattcca cntcacttgt gttccttcta    900
tttgcatcct ccgn                                                      914
```

```
<210> SEQ ID NO 17
<211> LENGTH: 22
<212> TYPE: DNA
<213> ORGANISM: Artificial Sequence
<220> FEATURE:
<223> OTHER INFORMATION: Primer

<400> SEQUENCE: 17
cccttgctac cttttccttc ct                                             22

<210> SEQ ID NO 18
<211> LENGTH: 21
<212> TYPE: DNA
<213> ORGANISM: Artificial Sequence
<220> FEATURE:
<223> OTHER INFORMATION: Primer

<400> SEQUENCE: 18
ccgatgtgtc aacgcataag g                                              21

<210> SEQ ID NO 19
<211> LENGTH: 13
<212> TYPE: DNA
<213> ORGANISM: Artificial Sequence
<220> FEATURE:
<223> OTHER INFORMATION: Probe

<400> SEQUENCE: 19
tctcgcagtt ctc                                                       13

<210> SEQ ID NO 20
<211> LENGTH: 16
<212> TYPE: DNA
<213> ORGANISM: Artificial Sequence
<220> FEATURE:
<223> OTHER INFORMATION: Probe

<400> SEQUENCE: 20
atctcgaagt tctctc                                                    16

<210> SEQ ID NO 21
<211> LENGTH: 501
<212> TYPE: DNA
<213> ORGANISM: Solanum pimpinellifolium
<220> FEATURE:
<221> NAME/KEY: misc_feature
<222> LOCATION: (136)..(136)
<223> OTHER INFORMATION: n is a, c, g, or t
<220> FEATURE:
<221> NAME/KEY: misc_feature
<222> LOCATION: (281)..(281)
```

```
<223> OTHER INFORMATION: n is a, c, g, or t
<220> FEATURE:
<221> NAME/KEY: misc_feature
<222> LOCATION: (284)..(284)
<223> OTHER INFORMATION: n is a, c, g, or t
<220> FEATURE:
<221> NAME/KEY: misc_feature
<222> LOCATION: (386)..(386)
<223> OTHER INFORMATION: n is a, c, g, or t
<220> FEATURE:
<221> NAME/KEY: misc_feature
<222> LOCATION: (391)..(391)
<223> OTHER INFORMATION: n is a, c, g, or t

<400> SEQUENCE: 21
tcagacctct ccgccattct ctccttcaaa aatgccttca cttcccttct agatactact    60
tacctttttt tcggaaaata aaacaaccaa ccaactatgt atcaacttca atctattaga   120
gtcaattcta taatcngata tatccattta gctctatttg gatccatttc tttcttagat   180
actagatttc caaaaagaat gacgttcttt ggcatttaat caacaaactt gatcagctct   240
tggaagtatc acaaactaga acaaacccat ttcataattc ngcnccatga caaatatcta   300
cacacaaatg acacatctat tgtccatatg aaaaatcraa gaatgaacca aacttgcaat   360
tataagtgag acatatatga agcatngaga naatgaaata cacttaagta cctagaaatt   420
aaacaaaagg tggtggtggt tttaccattg cagtttcgta agattctaat tagaagtcag   480
ctataagaat cctgggtgtc c                                            501

<210> SEQ ID NO 22
<211> LENGTH: 30
<212> TYPE: DNA
<213> ORGANISM: Artificial Sequence
<220> FEATURE:
<223> OTHER INFORMATION: Primer

<400> SEQUENCE: 22
catgacaaat atctacacac aaatgacaca                                    30

<210> SEQ ID NO 23
<211> LENGTH: 31
<212> TYPE: DNA
<213> ORGANISM: Artificial Sequence
<220> FEATURE:
<223> OTHER INFORMATION: Primer

<400> SEQUENCE: 23
ccaccacctt ttgtttaatt tctaggtact t                                  31

<210> SEQ ID NO 24
<211> LENGTH: 20
<212> TYPE: DNA
<213> ORGANISM: Artificial Sequence
<220> FEATURE:
<223> OTHER INFORMATION: Probe

<400> SEQUENCE: 24
atatgaaaaa tcgaagaatg                                               20

<210> SEQ ID NO 25
<211> LENGTH: 20
<212> TYPE: DNA
<213> ORGANISM: Artificial Sequence
<220> FEATURE:
<223> OTHER INFORMATION: Probe

<400> SEQUENCE: 25
```

```
atatgaaaaa tcaaagaatg                                                  20

<210> SEQ ID NO 26
<211> LENGTH: 602
<212> TYPE: DNA
<213> ORGANISM: Solanum pimpinellifolium

<400> SEQUENCE: 26
tgtttgtata cgggcaattc gcaacaaaac aattttgtct ttctcattttt gtgggacata      60 tttccccaaa gactcatcgt atgggatacc agcataatag tctagaactt taggaggggc     120
aggagtgctg cctggggtat ttgaggaaga cttggggtcc ggagtcagtg rtacagaaat     180
atttgtgttt acagcaggca atgcacaaac agtatcttgg gtcgctggca cactagccgt     240
ttcacttgaa ggtgcaatgg aggggtaggt gcttgaacta tgagaactgc ctacttctaa     300
agggccattg catttaactg tagtagttac cttagagtta gtactcttca ttgcgagacc     360
agaagaacaa gattcagagt tcagcgtctt gtccaaaacc atactgctcc aggtggtgag     420
ttttgcttta aaggaaccct tacccatacg acctttatag cttttctcaa aatgaaatgt     480
cttttgtcta agcatatctt tcttggagat catagaagac cccttctcc cagttccatt      540 tttttcttct aaaattgctg ctttcgttat agacagtaca ctctctccgc taaccctgc     600 ag                                                                     602
```